US012611493B2

(12) United States Patent
Kammerzell et al.

(10) Patent No.: US 12,611,493 B2
(45) Date of Patent: Apr. 28, 2026

(54) EXTRACORPOREAL BLOOD TREATMENT DEVICE WITH FUNCTION-MONITORING SYSTEM

(71) Applicant: PULSION MEDICAL SYSTEMS SE, Feldkirchen (DE)

(72) Inventors: Sergej Kammerzell, Munich (DE); Mark Konrad, Munich (DE)

(73) Assignee: Pulsion Medical Systems SE, Feldkirchen (DE)

( * ) Notice: Subject to any disclaimer, the term of this patent is extended or adjusted under 35 U.S.C. 154(b) by 930 days.

(21) Appl. No.: 17/427,073

(22) PCT Filed: Jan. 30, 2020

(86) PCT No.: PCT/EP2020/052336
  § 371 (c)(1),
  (2) Date: Apr. 18, 2022

(87) PCT Pub. No.: WO2020/157224
  PCT Pub. Date: Aug. 6, 2020

(65) Prior Publication Data
  US 2022/0249751 A1    Aug. 11, 2022

(30) Foreign Application Priority Data
  Jan. 31, 2019    (DE) .......................... 102019000732.8

(51) Int. Cl.
  *A61M 1/14*    (2006.01)
  *A61M 1/16*    (2006.01)

(52) U.S. Cl.
  CPC ............ *A61M 1/153* (2022.05); *A61M 1/154* (2022.05); *A61M 1/155* (2022.05);
  (Continued)

(58) Field of Classification Search
  CPC .............. A61M 1/3623; A61M 1/1698; A61M 1/1617; A61M 1/3609; A61M 2205/3368; G16H 40/63
  See application file for complete search history.

(56) References Cited

U.S. PATENT DOCUMENTS 4,941,475 A * 7/1990 Williams ............... A61B 5/028
                                                          600/549
5,526,817 A    6/1996 Pfeiffer et al.
              (Continued)

FOREIGN PATENT DOCUMENTS

DE        4214402 A1    11/1993
WO        0130237 A1    5/2001

OTHER PUBLICATIONS

Dornia et al., D-dimers Are a Predictor of Clot Volume Inside Membrane Oxygenators During Extracorporeal Membrane Oxygenation, Artificial Organs, vol. 29, No. 9, 2015, pp. 782-787.
(Continued)

*Primary Examiner* — Leslie R Deak
*Assistant Examiner* — Peter Daniel Smith
(74) *Attorney, Agent, or Firm* — Patterson + Sheridan, LLP; Carleton S. Clauss

(57) ABSTRACT

An extracorporeal blood treatment device with a function-monitoring system, wherein the extracorporeal blood treatment device for connection to the vascular system of a patient has an input branch and an output branch. The extracorporeal blood treatment device is equipped, in a first circuit, with at least one first pump arranged between the input branch and output branch for moving the patient's blood, and, in a second circuit filled with liquid and thermally connected to the first circuit of the extracorporeal blood treatment device via a heat exchanger, it has temperature-influencing means. The function-monitoring system has, in the second circuit, two temperature sensors which are arranged upstream ($TS2_{auf}$) and downstream ($TS2_{ab}$), respectively, with respect to the heat exchanger, in addition, temperature sensor $TS1_{ab}$ is arranged in the output branch of the first circuit, downstream from the heat exchanger. The function-monitoring system moreover comprises a computer system which is operatively connected to the aforemen-
(Continued)

tioned temperature sensors and the temperature-influencing means and which, after the temperature has been influenced, establishes, from the detected temperature values, corresponding thermodilution curves ($TDK1_{ab}$, $TDK2_{ab}$, $TDK2_{auf}$) and, in order to determine an indicator of the function of the extracorporeal blood treatment device, relates the $TDK2_{ab}$ and the $TDK_{1ab}$ to each other.

17 Claims, 1 Drawing Sheet

(52) U.S. Cl.
CPC ........ *A61M 1/1617* (2014.02); *A61M 1/1698* (2013.01); *A61M 2205/3368* (2013.01); *A61M 2205/3673* (2013.01)

(56) References Cited

U.S. PATENT DOCUMENTS

| 6,187,199 | B1 | 2/2001 | Goldau | |
| 6,394,961 | B1 | 5/2002 | Pfeiffer et al. | |
| 6,537,230 | B1 | 3/2003 | Pfeiffer et al. | |
| 2006/0030917 | A1* | 2/2006 | Eccleston | A61M 5/44 |
| | | | | 607/113 |
| 2011/0208106 | A1 | 8/2011 | Levin et al. | |
| 2012/0298581 | A1 | 11/2012 | Wehmeyer et al. | |
| 2015/0316404 | A1* | 11/2015 | Krivitski | G01F 22/02 |
| | | | | 702/19 |

OTHER PUBLICATIONS

German Patent Office, Office Action for German Patent Application No. 10 2019 000 732.8, dated Nov. 12, 2019.

* cited by examiner

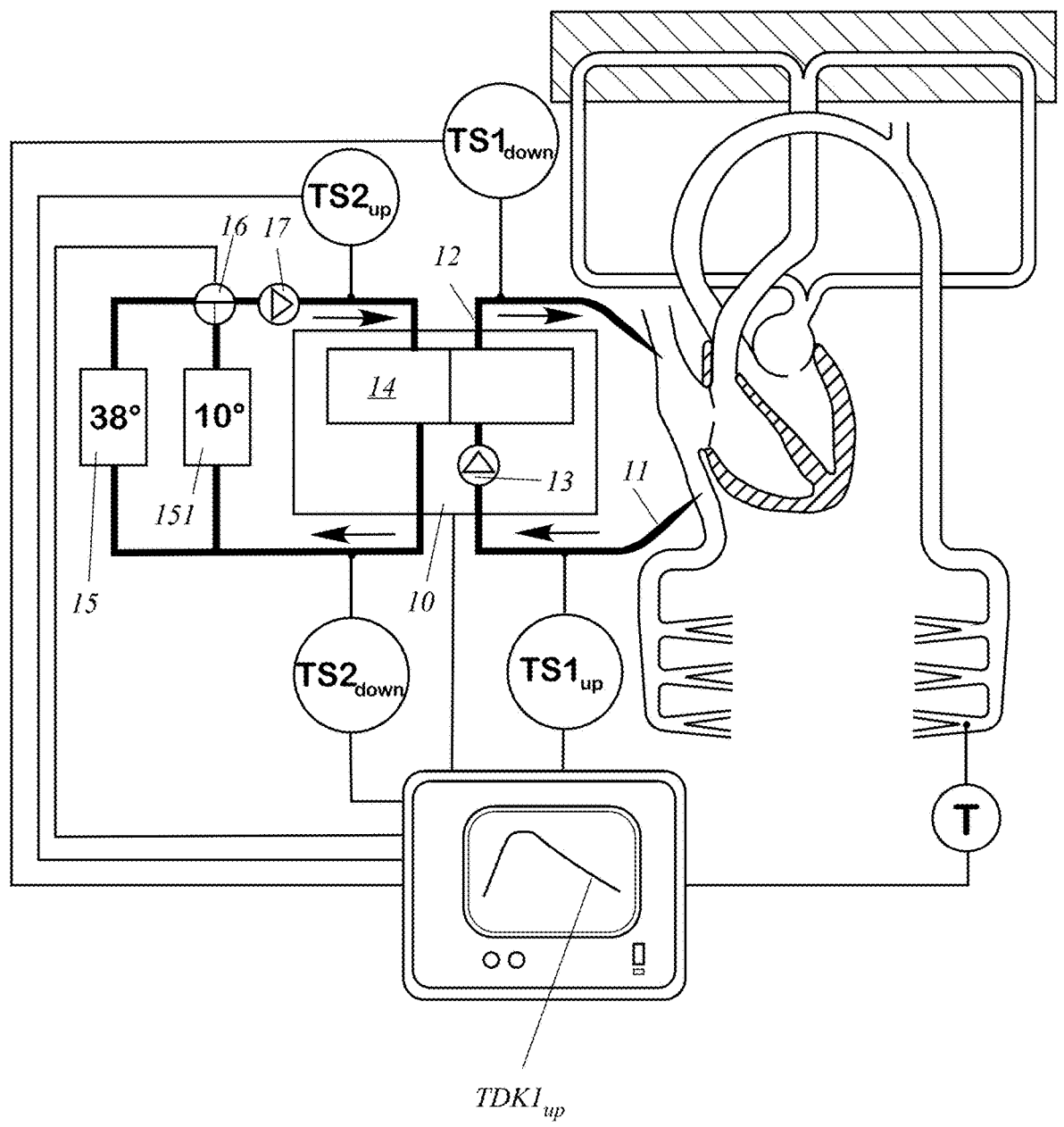

EXTRACORPOREAL BLOOD TREATMENT DEVICE WITH FUNCTION-MONITORING SYSTEM

CROSS-REFERENCE TO RELATED APPLICATIONS

This application is the United States national phase application of International Application No. PCT/EP20201052336, filed Oct. Jan. 30, 2020, which is incorporated herein by reference in its entirety. This application claims priority under 35 USC 119 to German Patent Application No. 102019000732.8, filed Jan. 31, 2019, the disclosure of which is incorporated by reference in its entirety.

BACKGROUND OF THE DISCLOSURE

Technical Field of Disclosure

The present disclosure relates to an extracorporeal blood treatment device with a function-monitoring system, a method for monitoring the functional state of an extracorporeal blood treatment device, and a computer system and a computer-readable storage medium for performing the method.

Description of Related Art

Extracorporeal blood treatment is indicated for a number of disorders in patients, for example hemodialysis or hemofiltration for kidney and liver diseases and extracorporeal membrane oxygenation (ECMO) in the treatment of severe lung diseases (acute respiratory distress syndrome, ARDS) and heart diseases (myocardial infarction, severe arrhythmias). Hemodialysis as part of renal replacement therapy involves the extracorporeal cleansing of the patient's blood of blood constituents that are excreted through the kidneys in a healthy person. During hemodialysis, these so-called "urinary" blood constituents are diffusively transported from the blood into a dialysis fluid via a semipermeable membrane. In contrast, during hemofiltration, substances are transported in a convective manner via a semipermeable filter membrane, wherein a pressure gradient on the membrane is the driving force for transporting the substances. Hemodiafiltration combines both principles, in that smaller molecules are removed from the blood using diffusion and larger substances using convection, thus generally increasing the total elimination rate for urinary substances.

Extracorporeal membrane oxygenation in the context of severe lung diseases is part of the standard therapy for stabilizing the circulation and/or respiratory function of patients with ARDS and life-threatening hypoxemia. In the ECMO device, the blood is perfused by means of a pump using a membrane oxygenator. The latter houses a semipermeable membrane via which the gas exchange takes place in that the blood of the patient flows on one side and oxygen is introduced on the other side. The pump produces a blood flow of 2 to 6 L/min, so that efficient oxygenation and elimination of carbon dioxide is possible.

When monitoring such a blood treatment, it is Important to detect the performance of the blood treatment. In the case of blood cleansing, for example by means of hemodialysis or hemofiltration as part of kidney or liver replacement therapy, blood cleansing performance is usually monitored using certain parameters; for example, the "clearance" determined in the context of hemodialysis indicates the hypothetical portion of the blood flow from which a certain substance is completely eliminated per minute. However, blood treatment performance during hemodialysis is only partially determined by the clearance value. In general, blood treatment performance of devices in which the blood is treated via a membrane depends on a number of factors, e.g. the membrane surface area in the treatment device, the permeability of the membrane, the flow rate of the blood within the treatment device, and/or the exchange fluid, e.g. the dialysis fluid in a hemodialyzer. The efficiency of the blood treatment decreases over time, e.g., due to the membrane of the blood treatment device becoming clogged. For example, the maximum service life of a hemofiltration membrane comprising hollow fibers for removing fluid and toxins in renal replacement therapy due to small blood clots (thrombi) being deposited in the lumina of the fibers may be only 15-40 hours. In the membrane of an oxygenator, as well, there can be a decrease in efficiency due to antibody (blood protein) deposits on the gas/blood membrane, since the gas/blood membrane clogs and thus the gas exchange capacity of the membrane is reduced. The reduced efficiency leads to a reduction in the oxygen supply to the blood to less than 100%. The thrombosis of the membrane via which the blood is treated usually occurs slowly over a variable period of a few hours. In conventional blood treatment devices, a functional disturbance is detected more or less early via the change in the systemic pressure conditions, via the drop in treatment performance, and also optically via detection of clots (thrombi) forming in the device. The determination of so-called D-dimers, which result due to the plasmin-mediated proteolysis of cross-linked fibrin in a thrombus, is a sensitive technique for early detection of a functional disturbance in the membrane of a blood treatment device. It is a drawback that determining these degradation products requires repeated removal of blood from the system and is therefore technically complex and expensive.

There is therefore a need to efficiently and continuously monitor the efficiency of the blood treatment at the membrane level, for example to monitor the membrane of a device for extracorporeal membrane oxygenation, in order to adjust the treatment process appropriately at the earliest possible point in time, to maximize the service life of the membrane, and to avoid possible harm to the patient.

BRIEF SUMMARY OF THE DISCLOSURE

In a first aspect, the disclosure relates to an extracorporeal blood treatment device having a function-monitoring system. The extracorporeal blood treatment device (EBTD) can be, for example, a device for hemodialysis, a device for liver support, or an extracorporeal device for decarboxylation or membrane oxygenation. For connection to the vascular system of a patient, the EBTD has an afferent line and an efferent line, wherein the afferent line of the blood treatment device supplies blood from the vascular system of the patient; the treated blood is returned to the patient's vascular system via the efferent line. For example, during purely venous extracorporeal membrane oxygenation (veno-venous ECMO, vvECMO), a drainage catheter located in the inferior vena cava leads venous blood to the membrane oxygenator, and a catheter located in the jugular vein or in the superior vena cavaleads oxygen-rich blood to the right atrium (or vice versa). In a first circuit, the disclosed EBTD includes at least one first pump arranged between the afferent line and the efferent line for moving the patient's blood. The pump conveys the blood through the corresponding treatment unit, for example the dialysis membrane or the decarboxytator/oxygenator membrane. The pump can be any type of pump known from the prior art, for example a roller pump or a centrifugal pump; the pump is preferably a centrifugal pump, since this reduces damage to corpuscular components of the blood and, subsequently, the release of coagulant substances. The pump can move the patient's blood through the first circuit at a constant and/or variable speed. Furthermore, the EBTD includes temperature-influencing means in a second liquid-filled circuit that is thermally connected to the first circuit of the EBTD via a heat exchanger. A heat exchanger (heat transfer apparatus) is understood to mean a device which transfers thermal energy from one substance flow to another; the disclosed heat exchanger transfers the thermal energy of the liquid circulating in the second circuit to the liquid of the first circuit separated therefrom by the heat-permeable wall of the heat exchanger (indirect heat transfer). According to the present disclosure, the heat exchanger can work with an undirected flow direction ("diffuse flow"), according to the countercurrent principle or according to the cocurrent principle; the heat exchanger preferably works with an undirected flow direction or according to the countercurrent principle. The temperature influencing means according to the present disclosure are configured to influence a temperature of the liquid in the second circuit in order to influence a temperature of the liquid in the first circuit via heat flow (via the heat exchanger). The term "influencing" is understood to mean both a (significant) change in temperature, for example from room temperature to OC, and a modulation of the temperature, for example a temperature deviation of 5°–10° C. about a mean value. In particular, the temperature influencing means in the second circuit generate a temperature change, particularly preferably a temperature bolus, i.e. a traveling temperature deviation with a rapid rise and fall in order to bring the temperature change to the level of the maximum temperature change in a minimum time. The temperature influencing means can be configured as means for influencing thermal energy known from the prior art, for example as a heat source or as a heat sink in the form of a Peltier element or a water bath that is temperature-controlled and/or temperature-controllable as required.

The disclosed function-monitoring system includes a temperature sensor $TS2_{up}$ arranged in the second circuit upstream of the heat exchanger and a temperature sensor $TS2_{down}$ arranged in the second circuit downstream of the heat exchanger. Furthermore, the function-monitoring system includes a temperature sensor $TS1_{down}$ arranged in the efferent line of the first circuit of the EBTD downstream of the heat exchanger. The terms "downstream" and "upstream" relate to the respective flow directions of the first and second circuits in the heat exchanger. Different sensor arrangements can result depending on the arrangement of the EBTD (flow direction of the patient's blood in the first circuit) and the mode of operation of the heat exchanger (co-current principle, countercurrent principle, undirected current flow); if, e.g., a cylindrical heat exchanger works according to the countercurrent principle, the downstream temperature sensors of the first and second circuits $TS1_{down}$ and $TS2_{down}$ can be located further apart from one another with respect to the heat exchanger (e.g., at opposite ends of the heat exchanger); if the heat exchanger works according to the co-current principle, the downstream temperature sensors $TS1_{down}$ and $TST2_{down}$ of the first and second circuits can be disposed close to one another with respect to the heat exchanger (e.g., at the same end of the heat exchanger). The temperature sensors provided can advantageously be configured like known sensors used in dilution measurement methods. A platinum resistance sensor is particularly suitable for measuring the temperature, but other thermoresistors or thermocouples are also suitable. A computer system connected to the temperature sensors ($TS2_{up}$, $TS2_{down}$, $TS1_{down}$) and the temperature influencing means and belonging to the function-monitoring system is configured to use the temperature influencing means to induce a temperature bolus in the first circuit of the EBKV, to record the temperatures $T2_{up}$, $T2_{down}$, $T1_{down}$ detected at the temperature sensors ($TS2_{up}$, $TS2_{down}$, $TS1_{down}$), respectively, as a function of time, and to determine and evaluate thermodilution curves (TDK) accordingly. Computer programs for carrying out evaluation steps of a thermodilution are known per se from the prior art (e.g., from German laid-open specification DE 42 14 402 A1). The disclosed computer system is further designed to relate the $TDK2_{down}$ and the $TDK1_{down}$ to one another and to determine an indicator of the EBTD function from the relationship of the $TDK2_{down}$ and $TDK1_{down}$.

In a further embodiment, the computer system can be configured to relate the $TDK2_{up}$ and the $TDK1_{up}$ to one another and to determine a further indicator of the EBTD function from the relationship of $TDK2_{up}$ and $TDK1_{down}$.

According to one advantageous enhancement, the function-monitoring system can furthermore have a temperature sensor ($TS1_{up}$) arranged in the afferent line of the first circuit of the EBTD upstream of the heat exchanger, wherein the indicator of the EBTD function is corrected by means of a correction factor from the relationship of $TDK2_{up}$ and the temperature $T1_{up}$ detected by the temperature sensor $TS1_{up}$ or possibly a variable derived therefrom, e.g. the $TDK1_{up}$.

The temperature change generated by the temperature influencing means in the first circuit, in particular a temperature bolus, can be estimated from the difference of the $TDK2_{up}$ and the $TDK2_{down}$ and reflects the amount of heat that can be transferred through the heat exchanger (heat transfer apparatus) from the second circuit of the EBTD into the first circuit and ultimately into the patient's circulation. With a high temperature gradient between the bolus temperature ($T2_{up}$, e.g. 10° C.) and the blood temperature in the afferent line ($T1_{up}$, e.g. 38° C.), a large amount of heat is transferred from the second circuit to the first circuit, and the maximum temperature measured at $TS1_{down}$. (or the "area under the curve" (AUC) of $TDK1_{down}$) largely corresponds to the value measured at $TS2_{down}$ (or the AUC of the $TDK2_{down}$). If there is a malfunction of the EBTD, for example due to a reduction in the exchange surface area of the oxygenator membrane as a result of local blood clotting ("membrane clotting"), less heat is emitted via the membrane; even with a high temperature gradient, if the function is impaired ("clogging" of the membrane by blood clots) only a small amount of heat is transferred to the temperature sensor $TS1_{down}$ located in the efferent line of the first circuit of the EBTD; the maximum temperature measured there (or the AUC of the $TDK1_{down}$) can be less than the value measured at temperature sensor $TS2_{down}$. If functioning is not impaired (free membrane surface), when the temperature gradient between the first and second circuits is high, a large amount of heat is emitted and is passed on in the first circuit via temperature sensor $TS1_{down}$, i.e. the maximum temperature measured at $TS1_{down}$, (or the AUC or $TDK1_{down}$) corresponds to the value measured at $TS2_{down}$ (or the AUC of $TDK2_{down}$).

Optionally taking additionally into account a correction factor from the relationship of the $TDK2_{up}$ and the temperature $T1_{up}$ detected by the temperature sensor $TS1_{up}$ permits a more accurate determination of the indicator. For example, the computer system can record the temperature $T1_{up}$ currently detected by temperature sensor $TS1_{up}$ as a function of time and accordingly generate the thermodilution curve $TDK1_{up}$. The initial temperature gradient between the two circuits can be derived from the ratio $TDK2_{up}/TDK1_{up}$ and can be used for correcting the relationship of $TDK2_{down}$ and $TDK1_{down}$. Furthermore, the relationship of the temperature value measured by the additional temperature sensor $TS1_{up}$ in connection with $TDK1_{down}$ can be used to determine a temperature deviation to be assigned to the extracorporeal blood treatment device (as a measure of the recirculation).

The indicator of the EBTD function determined from the relationship of $TDK2_{down}$ and $TDK1_{down}$, or the further indicator of the EBTD function determined from the relationship of $TDK2_{up}$ and $TDK1_{down}$, can be used to reliably determine the functional state of the functional unit arranged in the blood treatment device, namely of the membrane used for the treatment (e.g. dialysis membrane, filtration membrane, decarboxylator/oxygenator membrane). For example, the functional state can be determined using a simple ratio relation $TDK2_{down}/TDK1_{down}$; a shift in the ratio toward $TDK2_{down}$ indicates a disturbance in the membrane function, the magnitude of the shift in the ratio indicating the extent of the disturbance in the membrane function. Advantageously, all measurements may be carried out automatically in the device by means of the function-monitoring system according to the disclosure; no additional functional units or method steps are required. In addition, compared to conventional monitoring methods using pressure or flow measurement, the system is sensitive to small changes in the EBTD function, e.g. functional restrictions of the oxygenator membrane in an ECMO.

In a further implementation of the device according to the disclosure, the computer system can be configured to control at least one second pump connected to the temperature influencing means in the second circuit such that the pump speed is adjusted to generate a substantially sharp temperature difference; the temperature difference relates in particular to the difference between the temperature of the liquids in the first circuit and the second circuit, respectively, in the region of the heat exchanger. Particularly preferably, the second pump can be arranged in the second circuit upstream of the heat exchanger. The second pump in the second circuit can preferably run at a higher speed than the first pump in the first circuit during the heat transfer. For example, the disclosed computer system can be configured to detect data from the first pump in the first circuit, e.g., a set speed or the flow resulting from the set speed (e.g., by means of a flow sensor arranged in the first circuit). For monitoring the function of the EBTD, the ratio of the corresponding pump speeds to one another can advantageously be the same for the respective measurement, so that an automated measurement is possible.

In one advantageous enhancement, the temperature influencing means can generate a temperature bolus in the first circuit of the EBTD. A temperature bolus is understood to mean a temperature which differs relative to the temperature of the first circuit/blood circulation of the patient and which is characterized by a rapid rise and a rapid drop. The temperature deviation can involve the introduction of heat or cold. The thermal unit used in a conventional EBTD keeps the patient's blood temperature largely constant, at 37-39° C., during treatment; a sharp temperature difference for a cold bolus can be generated for a limited time by the disclosed computer system controlling at least one further unit, e.g., a cooling unit of the temperature influencing means. The EBTD implemented accordingly can also be used to carry out thermodilution measurements in the patient, for example to determine hemodynamic/cardiovascular parameters, without the need for applying a temperature bolus to a further location in the patient's vascular system.

In one further embodiment, the temperature influencing means can be arranged downstream of the first pump. In this embodiment, the function-monitoring system can be connected to a blood treatment device in a simple manner.

In one preferred implementation of the device according to the disclosure, the temperature influencing means can include switching means for switching between at least two temperatures. If the temperature influencing means are configured, for example, as a water bath with containers of different temperatures, the container with the desired temperature can be connected to the second circuit by means of the switching means. Alternatively, e.g., in the case of temperature influencing means designed as a Peltier element, the switching means can switch the supply of the means or of the second circuit to which thermal energy is applied to the heat exchanger, possibly thereby also the connection to the first circuit. Particularly preferably, the switching means can also switch the temperature influencing means on and off. In one particularly advantageous enhancement, the switching means can switch between at least two liquid reservoirs at different temperatures, for example between a reservoir with a temperature equal to the temperature in the first circuit and a reservoir with a temperature differing therefrom by at least 10° C.

In one further embodiment of the device according to the disclosure, the EBTD can be a device for extracorporeal membrane oxygenation (ECMO). In one particularly preferred enhancement of the blood treatment device according to the disclosure, the temperature influencing means can be arranged in the region of the oxygenator of the ECMO. The term "in the region" refers to a close spatial relationship; this is advantageous in order to keep the dimensions of the ECMO as small as possible. Continuous function monitoring of the oxygenator membrane is indicated, particularly with ECMO, since in seriously ill patients a functional disturbance of the membrane due to thrombus formation can lead not only to reduced gas exchange, but also to a clotting disorder in the patient after the functional disturbance in the membrane (Domia et al., 2015).

In one preferred implementation of the disclosed device, the temperature influencing means can be connected externally to a heating unit of the EBTD. For example, temperature influencing means designed as a Peltier element can be connected to corresponding inlets or outlets of the heating unit of the EBTD. In this way, an EBTD without a function-monitoring system can advantageously be retrofitted in a simple manner.

In a second aspect, the present disclosure relates to a method for monitoring the functional state of an extracorporeal blood treatment device as described above. In a first step of the method, a temperature bolus is induced in the second circuit of the EBTD, wherein the temperature difference underlying the temperature bolus is caused by means of the temperature influencing means of the second circuit of the EBTD, wherein the first circuit of the EBTD is thermally connected to the second circuit of the EBTD via a heat exchanger. In a second step, a temperature $T2_{up}$ is detected upstream of the heat exchanger in the second circuit of the EBTD by means of a first temperature sensor $TS2_{up}$, while in a subsequent third step a temperature $T2_{down}$ is detected in the second circuit of the EBTD by means of a temperature sensor $TS2_{down}$ arranged downstream of the heat exchanger and a temperature $T1_{down}$ is detected in the efferent line of the first circuit of the EBTD by means of a temperature sensor $TS1_{down}$ arranged downstream of the heat exchanger. In a further, fourth step, an indicator of the EBTD function is determined by relating the thermodilution data $TDK2_{down}$ and $TDK1_{down}$ determined from the temperatures $T2_{down}$ and $T_{down}$ detected by the temperature sensor $TS2_{down}$ and temperature sensor $TS1_{up}$.

In a further implementation of the method according to the disclosure, a further indicator of the EBTD function can be determined in an additional step by relating the thermo-dilution data $TDK2_{up}$ and $T_{down}$ determined from the temperatures $T2_{up}$ and $T1_{down}$ detected by temperature sensor $TS2_{up}$ and temperature sensor $TS1_{up}$.

In a preferred embodiment of the method according to the disclosure, an additional step can be included in which a further temperature in the first circuit can be detected, specifically via the temperature sensor $TS1_{up}$ arranged upstream of the heat exchanger in the afferent line of the first circuit of the EBTD, and there can be a correction of the indicator of the EBTD function by means of a correction factor from the relationship of a $TDK2_{up}$ and the temperature $T1_{up}$ detected by the temperature sensor $TS1_{up}$.

In a third aspect, the present disclosure relates to a computer system which is configured to interact with an extracorporeal blood treatment device with a function-monitoring system as described above, the computer system having the following: Connection means for connecting the computer system to the temperature sensors $TS2_{up}$, $TS2_{down}$, $TS1_{up}$ and the temperature influencing means, and access means for accessing executable commands for causing the computer system to control temperature influencing means in the second circuit of the EBTD to initiate a temperature bolus in the second circuit of the EBTD. The access means also cause the computer system to record each of the temperatures $T2_{up}$, $T2_{down}$, $T_{down}$ detected at the temperature sensors $TS2_{up}$, $TS2_{up}$, $TS1_{down}$ as a function of time and to determine and evaluate thermodilution curves (TDK) accordingly, as well as to relate $TDK2_{down}$ and $TDK1_{down}$ to one another and to determine an indicator of the EBTD function from the relationship of $TDK2_{down}$ and $TDK1_{down}$.

In a fourth aspect, the disclosure relates to a non-volatile, computer-readable storage medium with computer-readable instructions for determining an indicator of the function of an extracorporeal blood treatment device with a function-monitoring system as described above, wherein the computer-readable instructions are executable by a computer system in order to cause the computer system to control temperature influencing means in the second circuit of the EBTD to cause a temperature bolus in the second circuit of the EBTD such that said computer system records each of the temperatures $T2_{up}$, $T2_{down}$, $T1_{down}$ at the temperature sensors $TS2_{up}$, $TS2_{down}$, $TS1_{down}$ as a function of time and accordingly determines and evaluates thermodilution curves (TDK), and such that said computer system relates the $TDK2_{down}$ and the $TDK1_{down}$ to one another and determines an indicator of the EBTD function from the relationship of the $TDK2_{down}$ and $TDK1_{up}$.

As used herein, the singular form of the articles "a" and "the" includes the corresponding plural forms unless otherwise specified. For example, the expression "a liquid reservoir" includes a corresponding reservoir or a plurality of reservoirs.

One particularly preferred embodiment of the present disclosure is explained in more detail in the following with reference to the associated drawing, but the disclosure is not limited thereto. In principle, every variant of the disclosure described or suggested in the context of the present application can be particularly advantageous, depending on the economic, technical and possibly medical conditions in an individual case. Unless stated to the contrary, or as far as technically feasible in principle, individual features of the embodiments described are interchangeable or can be combined with one another and with features known per se from the prior art.

BRIEF DESCRIPTION OF THE FIGURE

The drawing is purely schematic and, for illustrative reasons, is not true to scale. In particular, the relationships between the dimensions, especially diameters, tube lengths, and external dimensions may differ from actual embodiments. In practice, the dimensions can be dimensioned based on the requirements in individual cases and based on common standard parts.

FIG. 1 shows a schematic overview of the disclosed extracorporeal blood treatment device with a function-monitoring system, wherein the interaction with the vascular system of a patient is shown for purposes of illustration.

PREFERRED EMBODIMENT OF THE DISCLOSURE

FIG. 1 shows a schematic overview of the disclosed extracorporeal blood treatment device with a function-monitoring system. The extracorporeal blood treatment device (EBTD, 10) is connected to the venous vascular system of a patient via an afferent line (11) and an efferent line (12). The extracorporeal blood treatment apparatus can be, for example, a device for extracorporeal membrane oxygenation (veno-venous ECMO, vvECMO, as shown in FIG. 1) or a device for liver dialysis. The afferent line (11) is introduced, for example, via the femoral vein and comes to rest in the lower caval vein (V. cava inferior) below the convergence of the hepatic vein. The efferent line (12) is introduced, for example, via the jugular vein and comes to rest in the upper cval vein (V. cava superior) immediately in front of the right atrium. In the case of ECMO, low-oxygen, venous blood is supplied to the blood treatment device via the afferent line (11), while the oxygenated blood reaches the right atrium via the efferent line (12). The disclosed EBTD can also be used as an ECMO in situations in which the deoxygenated blood is conducted to the ECMO via the femoral vein and the oxygenated blood is returned to the vascular system of the patient via the femoral artery (vaECMO); in this arrangement, the ECMO can take over the entire pumping action in the patient's circulation in addition to the device circuit. For treatment, the patient's blood is conducted by means of a pump (13) over a membrane, for example a hemodialysis membrane, a hemofiltration membrane, a hemodiafiltration membrane, or an oxygenator membrane of an ECMO. Input and efferent lines, as well as the lines connected to the actual blood treatment device (membrane), form a first circuit. The pump (13), which is preferably embodied as a centrifugal pump, is used to control and regulate the circulation of the blood through the first circuit. The pumps used in an extracorporeal circuit of conventional blood treatment devices are usually connected to a control device and can thus be controlled directly so that these pumps can either provide a relatively constant flow rate or a variable flow rate through the extracorporeal circuit and the actual blood treatment device (membrane). In the disclosed EBTD with a function-monitoring system, in addition to the first circuit, which corresponds to the extracorporeal circuit of a conventional EBTD, a second circuit is provided which is thermally connected to the first EBTD circuit via a heat exchanger (14) and has temperature influencing means (15). The transfer of thermal energy takes place via the heat-permeable wall of the heat exchanger, which separates the first circuit and the second circuit from one another (indirect heat exchange). In the embodiment shown, the heat exchanger (14) operates according to the countercurrent principle, but the mode of operation with a diffuse flow direction is preferred as well. The temperature influencing means (15) are set up to influence the temperature of the liquid in the second circuit in order to influence the temperature in the first circuit (patient's blood) via heat flow (heat exchanger). The temperature influencing means can have a heating device which is set up to supply thermal energy in the form of heat to the second circuit; alternatively, the temperature influencing means can also have a cooling device which is set up to withdraw thermal energy from the second circuit. In the embodiment shown, the temperature influencing means (15) use a liquid, preferably water, for heating/cooling the liquid of the second circuit; as shown, a reservoir (151) filled with cold water can be connected to the second circuit via switching means (16). A second pump (17) arranged in the second circuit is set up to circulate the liquid in the second circuit. The disclosed EBTD includes a function-monitoring system for determining an indicator of the EBTD function. The system is suitable in particular for monitoring the function of the membrane used for the blood treatment. The functional monitoring system includes a temperature sensor $TS2_{up}$ arranged in the second circuit upstream of the heat exchanger (14) and a temperature sensor $TS2_{down}$ arranged in the second circuit downstream of the heat exchanger (14). Furthermore, a temperature sensor $TS1_{down}$ arranged in the first circuit downstream of the heat exchanger belongs to the functional monitoring system. The terms "downstream" and "upstream" relate to the respective flow directions of the first circuit and second circuit in the heat exchanger. If the heat exchanger operates according to the countercurrent principle, the flow directions of the liquids in the first and second circuit are opposite; if the heat exchanger operates according to the cocurrent principle, the flow directions of the liquids in the first circuit and second circuit are the same. In the case of a heat exchanger operating with undirected flow, there is also an upstream input into the heat exchanger and a downstream outlet out of it. In the present embodiment, the temperature sensor $TS1_{up}$ is arranged in the afferent line (11) of the first circuit upstream of the heat exchanger (14) of the EBTD. The computer system (40) connected to the temperature sensors $TS1_{down}$, $TS1_{up}$, $TS2_{down}$, $TS2_{up}$ is designed to initiate a temperature bolus in the second circuit of the EBTD by means of the temperature influencing means (15). The computer system (40) is usefully connected to the switching means (16) and the pump (17) of the second circuit. In particular, the computer system can adjust the pump speed to generate a substantially sharp temperature bolus with regard to the heat exchanger. From the temperatures $T1_{down}$, $T1_{up}$, $T2_{down}$, $T2_{up}$ detected by the temperature sensors $TS1_{down}$, $TS1_{up}$, $TS2_{down}$, $TS2_{up}$, a temperature profile can be recorded in a known manner as a function of time and can be evaluated in a respective thermodilution curve. Furthermore, the computer system is designed to use the determined thermodilution curves (TDK) to relate $TDK2_{down}$ and $TDK1_{down}$ to one another and to determine an indicator of the EBTD function from the relationship of $TDK2_{down}$ and $TDK1_{down}$. The computer system may further be configured to relate $TDK2_{up}$ and $TDK1_{down}$ determined from the thermodilution curves (TDK) and to determine a further EBTD function from the relationship of $TDK2_{up}$ and $TDK1_{down}$. This particular indicator may be corrected by means of a correction factor from the relationship of $TDK2_{up}$ and the temperature $T1_{up}$ detected by temperature sensor $TS1_{up}$ in that the initial temperature gradient between the two circuits is derived from the ratio $TDK2_{up}/TDK1_{up}$ and is taken into account for correcting the ratio $TDK2_{down}/TDK1_{down}$.

As shown in FIG. 1, the preferred embodiments also permit the detection of a temperature deviation attributable to the extracorporeal blood treatment device in that the temperature value $T1_{up}$ measured by the additional temperature sensor $TS1_{up}$ is related to the $TDK1_{down}$ generated from the values of the temperature sensor $TS1_{down}$.

LIST OF REFERENCE SYMBOLS

10 Extracorporeal blood treatment device, EBTD
11 Afferent line of the EBTD
12 Efferent line of the EBTD
13 Pump in the first circuit
14 Heat exchanger
15 Temperature influencing means
151 Liquid reservoir, temperature influencing means
16 Switching means
17 Pump in the second circuit

The invention claimed is:

1. An extracorporeal blood treatment device having a function-monitoring system, wherein the extracorporeal blood treatment device comprises an afferent line and an efferent line for connecting to the vascular system of a patient, wherein in a first circuit the extracorporeal blood treatment device has at least one first pump arranged between the afferent line and the efferent line for moving the patient's blood, and comprises a temperature adjusting device in a second, liquid-filled circuit that is thermally connected to the first circuit of the extracorporeal blood treatment device by a heat exchanger, wherein the function-monitoring system comprises:
   a. a temperature sensor $TS2_{up}$ arranged in the second circuit upstream of the heat exchanger and a temperature sensor $TS2_{down}$ arranged in the second circuit downstream of the heat exchanger;
   b. a temperature sensor $TS1_{down}$ arranged in the efferent line of the first circuit of the extracorporeal blood treatment device downstream of the heat exchanger; and
   c. a computer system connected to the temperature sensors ($TS2_{up}$, $TS2_{down}$, $TS1_{down}$) and the temperature adjusting device, and configured to use the temperature adjusting device to induce a temperature bolus in the second circuit of the extracorporeal blood treatment device, to record the temperatures $T2_{up}$, $T2_{down}$, $TS1_{down}$ detected at the temperature sensors $TS2_{up}$, $TS2_{down}$, $TS1_{down}$, respectively, as a function of time and to determine and evaluate corresponding thermodilution curves (TDK), and is furthermore configured to relate $TDK2_{down}$ and $TDK1_{down}$ to one another and to determine an indicator of the extracorporeal blood treatment device function from a ratio of $TDK2_{down}$ and $TDK1_{down}$, and wherein the indicator of the functionality of the extracorporeal blood treatment device is an indicator of a functionality of a membrane in the extracorporeal blood treatment device.

2. The device according to claim 1, wherein the computer system is designed to relate $TDK2_{up}$ and $TDK1_{down}$ to one another and to determine a further indicator of the extracorporeal blood treatment device function from the relationship of $TDK2_{up}$ and $TDK1_{down}$.

3. The device according to claim 1, wherein the function-monitoring system further comprises a temperature sensor $TS1_{up}$ arranged in the afferent line of the first circuit upstream of the heat exchangers of the extracorporeal blood treatment device, wherein the indicator of extracorporeal blood treatment device function is corrected by a correction factor from the relationship of $TDK2_{up}$ and the temperature $T1_{up}$ detected by temperature sensor $TS1_{up}$.

4. The device according to claim 1, wherein the computer system is configured to control at least one second pump connected to the temperature adjusting device in the second circuit such that a pump speed is adjusted to generate a temperature difference.

5. The device according to claim 4, wherein the second pump is arranged in the second circuit upstream of the heat exchanger.

6. The device according to claim 1, wherein the temperature adjusting device generate a temperature bolus in the first circuit of the extracorporeal blood treatment device.

7. The device according to claim 1, wherein the temperature adjusting device are arranged downstream of the first pump.

8. The device according to claim 1, wherein the temperature adjusting device comprise a switch for switching between at least two temperatures.

9. The device according to claim 8, wherein the switch switches between at least two different temperature-controlled liquid reservoirs.

10. The device according to claim 1, wherein the extracorporeal blood treatment device is a device for extracorporeal membrane oxygenation.

11. The device according to claim 10, wherein the temperature adjusting device are arranged in the region of an oxygenator of the extracorporeal membrane oxygenation.

12. The device according to claim 1, wherein the temperature adjusting device are connected externally to a heating unit of the extracorporeal blood treatment device.

13. A method for monitoring a functional state of an extracorporeal blood treatment device according to claim 1, comprising:

a. Inducing a temperature bolus in the second circuit of the extracorporeal blood treatment device, wherein a temperature deviation underlying the temperature bolus is caused by the temperature adjusting device of the second circuit of the extracorporeal blood treatment device, wherein the first circuit of the extracorporeal blood treatment device is thermally connected to the second circuit of the extracorporeal blood treatment device via a heat exchanger;

b. Detecting a temperature $T2_{up}$ in the second circuit of the extracorporeal blood treatment device by a temperature sensor $TS2_{up}$ arranged upstream of the heat exchanger;

c. Detecting a temperature $T2_{down}$ in the second circuit of the extracorporeal blood treatment device by a temperature sensor $TS2_{down}$ downstream of the heat exchanger and detecting a temperature $T1_{down}$ in the efferent line of the first circuit of the extracorporeal blood treatment device by a temperature sensor $TS1_{down}$ arranged downstream of the heat exchanger; and d. Determining an indicator of a functionality of the extracorporeal blood treatment device by relating the thermodilution data $TDK2_{down}$ and $TDK1_{down}$ determined from the temperatures $T2_{down}$ and $T1_{down}$ detected by temperature sensor $TS2_{down}$ and temperature sensor $TS1_{down}$.

14. The method according to claim 13, additionally comprising the step:

d. Determining a further indicator of the functionality of the extracorporeal blood treatment device by relating the thermodilution data $TDK2_{up}$ and $TDK1_{down}$ determined from the temperatures $T2_{up}$ and $T1_{down}$ detected by temperature sensor $TS2_{up}$ and temperature sensor $TS1_{down}$.

15. The method according to claim 13, additionally comprising the steps:

e. Detecting a temperature in the afferent line of the first circuit of the extracorporeal blood treatment device by a temperature sensor $TS1_{up}$ arranged upstream of the heat exchanger, and correcting the indicator of the functionality of the extracorporeal blood treatment device by a correction factor from the relationship of a $TDK2_{up}$ and the temperature $T1_{up}$ detected by temperature sensor $TS1_{up}$.

16. A computer system configured to interact with an extracorporeal blood treatment device having a function-monitoring system according to claim 1, wherein the computer system comprises the following:

a connector for connecting the computer system to the temperature sensors $TS2_{up}$, $TS2_{down}$, $TS1_{down}$, and the temperature adjusting device, and executable commands stored in memory to cause the computer system:

a. to control a temperature adjusting device in the second circuit of the extracorporeal blood treatment device in order to induce a temperature bolus in the second circuit of the extracorporeal blood treatment device;

b. to record the temperatures $T2_{up}$, $T2_{down}$, $T1_{down}$ detected at the temperature sensors $TS2_{up}$, $TS2_{down}$, $TS1_{down}$, in each case as a function of time, and accordingly to detect and evaluate to thermodilution (TDK); and, c. to relate $TDK2_{down}$ and $TDK1_{down}$ to one another and determine an indicator of the functionality of the extracorporeal blood treatment device from a ratio of $TDK2_{down}$ and $TDK1_{down}$, and wherein the indicator of the functionality of the extracorporeal blood treatment device is an indicator of a functionality of a membrane in the extracorporeal blood treatment device.

17. A non-volatile, computer-readable storage medium with computer-readable instructions for determining an indicator of a functionality of an extracorporeal blood treatment device having a function-monitoring system according to claim 1, wherein the computer-readable instructions are executable by a computer system to cause the computer system:

a. to control a temperature adjusting device in the second circuit of the extracorporeal blood treatment device to induce a temperature bolus in the second cycle of the extracorporeal blood treatment device;

b. to record the temperatures $T2_{up}$, $T2_{down}$, $T1_{down}$ detected on the temperature sensors $TS2_{up}$, $TS2_{down}$, $TS1_{down}$, in each case as a function of time, and to determine and evaluate thermodilution curves (TDK) accordingly; and, c. to relate the $TDK2_{down}$ and the $TDK1_{down}$ to one another and to determine the indicator of the functionality of the extracorporeal blood treatment device from a ratio of $TDK2_{down}$ and $TDK1_{down}$, and wherein the indicator of the functionality of the extracorporeal blood treatment device is an indicator of a functionality of a membrane in the extracorporeal blood treatment device.

\* \* \* \* \*